United States Patent [19]

Chasin et al.

[11] Patent Number: 5,744,473
[45] Date of Patent: Apr. 28, 1998

[54] PDE IV INHIBITORS: "BIS-COMPOUNDS"

[75] Inventors: Mark Chasin, Manalapan, N.J.; Peter Hofer, Liestal, Switzerland; David Cavalla, Cambridge, United Kingdom

[73] Assignee: Euro-Celtique, S.A., Luxembourg, Luxembourg

[21] Appl. No.: 714,581

[22] Filed: Sep. 16, 1996

[51] Int. Cl.$^6$ .................. C07D 519/00; A61K 31/52; A61K 31/505; A61K 31/44
[52] U.S. Cl. .................. 514/262; 514/266; 544/276; 544/277; 544/253; 544/280; 546/112; 546/113; 546/183
[58] Field of Search .................. 544/276, 277; 514/262

[56] References Cited

U.S. PATENT DOCUMENTS

| | | | |
|---|---|---|---|
| 2,691,654 | 10/1954 | Hitchings | 260/247.5 |
| 2,844,577 | 7/1958 | Acker | 260/254 |
| 2,903,455 | 9/1959 | Strong et al. | 260/252 |
| 2,956,998 | 10/1960 | Baizer | 260/252 |
| 2,957,875 | 10/1960 | Lyttle et al. | 260/252 |
| 2,966,488 | 12/1960 | Shive et al. | 260/252 |
| 3,135,753 | 6/1964 | Hitchings | 540/265 |
| 3,136,771 | 6/1964 | Liechti et al. | 260/296 |
| 3,215,696 | 11/1965 | Denayer | 260/252 |
| 3,225,046 | 12/1965 | Zwahlen | 260/252 |
| 3,262,929 | 7/1966 | Okubu et al. | 260/240 |
| 3,494,919 | 2/1970 | Collins et al. | 260/240 |
| 3,541,100 | 11/1970 | Ramirez et al. | 260/286 |
| 3,574,218 | 4/1971 | Hideg et al. | 260/293.4 |
| 3,636,039 | 1/1972 | Gruenman et al. | 260/309.7 |
| 3,674,781 | 7/1972 | Schinzel et al. | 260/240 |
| 3,706,834 | 12/1972 | Scheilenbach et al. | 424/272 |
| 3,923,833 | 12/1975 | Gruenmann et al. | 260/340.5 |
| 3,962,452 | 6/1976 | Evans et al. | 424/272 |
| 4,025,636 | 5/1977 | Dunwell et al. | 424/269 |
| 4,025,637 | 5/1977 | Dunwell et al. | 424/272 |
| 4,167,628 | 9/1979 | Kormany | 542/454 |
| 4,308,278 | 12/1981 | Schneider et al. | 424/273 |
| 4,361,699 | 11/1982 | Rasmusson et al. | 544/277 |
| 4,416,892 | 11/1983 | Dawson | 424/272 |
| 4,652,654 | 3/1987 | Verga et al. | 548/217 |
| 4,684,656 | 8/1987 | Atwal | 514/274 |
| 4,710,503 | 12/1987 | Hofer | 514/263 |
| 4,803,216 | 2/1989 | Appleton et al. | 514/407 |
| 4,831,152 | 5/1989 | Itoh et al. | 548/224 |
| 4,868,183 | 9/1989 | Kanai et al. | 514/255 |
| 4,925,847 | 5/1990 | Hofer | 514/263 |
| 5,047,411 | 9/1991 | Takasugi et al. | 514/300 |
| 5,068,236 | 11/1991 | Suzuki et al. | 514/263 |
| 5,117,830 | 6/1992 | McAfee et al. | 128/654 |
| 5,190,942 | 3/1993 | Poss | 514/235.8 |
| 5,206,255 | 4/1993 | Ubsawa et al. | 514/374 |
| 5,264,589 | 11/1993 | Corey | 548/51 |
| 5,322,847 | 6/1994 | Marfat et al. | 514/303 |
| 5,496,853 | 3/1996 | Shiota et al. | 514/469 |

FOREIGN PATENT DOCUMENTS

| | | |
|---|---|---|
| 0178413 | 4/1986 | European Pat. Off. . |
| 0256692 | 2/1988 | European Pat. Off. . |
| 0343643 | 11/1989 | European Pat. Off. . |
| 0470805 | 2/1992 | European Pat. Off. . |
| 0497564 | 8/1992 | European Pat. Off. . |
| 0511865 | 11/1992 | European Pat. Off. . |
| 835818 | 2/1961 | France . |
| 1548252 | 12/1968 | France . |
| 51-54587 | 5/1976 | Japan . |
| 57-21375 | 2/1982 | Japan . |
| 215948 | 10/1989 | New Zealand . |
| 1077689 | 8/1967 | United Kingdom . |
| 1498705 | 1/1978 | United Kingdom . |
| 2041359 | 9/1980 | United Kingdom . |
| 8706576 | 4/1986 | WIPO . |
| 9219594 | 11/1992 | WIPO . |
| 9307111 | 4/1993 | WIPO . |

(List continued on next page.)

OTHER PUBLICATIONS

Leonard, J.A.C.S. 95, 4010 (1973).
Ronald E. Weishaar, et al., Subclasses of Cyclic GMP–Specific phosphodiesterase and their role in regulating the effects of atrial natriuretic factor, Dept. Of Pharmacology, Park–Davis Pharmaceutical Research Division, Warner–Lambert Co. Hypertension, vol. 15, No. 5, May 1990.

(List continued on next page.)

Primary Examiner—Mark L. Berch
Attorney, Agent, or Firm—Steinberg, Raskin & Davidson, P.C.

[57] ABSTRACT

Novel compounds which are effective PDE IV inhibitors are disclosed. The compounds possess improved PDE IV inhibition as compared to theophylline or rolipram, with improved selectivity with regard to, e.g., PDE V inhibition. Also provided is a process of making compounds of Formula I. Compounds of the present invention are represented by Formula I:

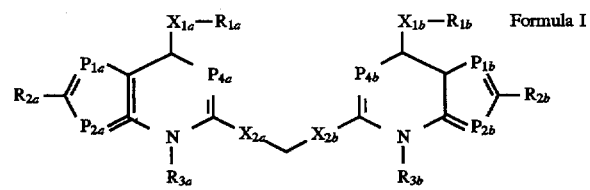

its pharmaceutically acceptable salts, hydrochloride salts, or prodrug forms thereof, wherein:

$X_{1a}$, $X_{1b}$ are independently selected from —NH and —N-lower alkyl;

$X_{2a}$, $X_{2b}$ are optionally present and are independently selected from $S(O)n$, O, $CH_2$, and NH;

$P_{1a}$, $P_{1b}$, $P_{2a}$, $P_{2b}$, $P_{4a}$, and $P_{4b}$ are independently selected from N, or CH;

$R_{1a}$, $R_{1b}$, $R_{2a}$, $R_{2b}$, $R_{3a}$ and $R_{3b}$ are independently selected from H, $C_1$–$C_6$ alkyl, $C_3$–$C_6$ branched alkyl, $C_3$–$C_6$ cycloalkyl, said alkyl groups being optionally substituted with halogen, aryl or heteroaryl group(s), said aryl and heteroaryl group(s) being optionally substituted with hydroxy, alkoxy, cycloalkoxy, halogen, alkyl, or cycloalkyl; and n is an integer from 0 to 2.

17 Claims, No Drawings

FOREIGN PATENT DOCUMENTS

| | | |
|---|---|---|
| 9314081 | 7/1993 | WIPO. |
| 9314082 | 7/1993 | WIPO. |
| 9315044 | 8/1993 | WIPO. |
| 9315045 | 8/1993 | WIPO. |
| 9319747 | 10/1993 | WIPO. |
| 9325517 | 12/1993 | WIPO. |
| 9402465 | 2/1994 | WIPO. |
| 9410118 | 5/1994 | WIPO. |
| 9412461 | 6/1994 | WIPO. |
| 9414742 | 7/1994 | WIPO. |
| 9414800 | 7/1994 | WIPO. |
| 9420446 | 9/1994 | WIPO. |
| 9420455 | 9/1994 | WIPO. |

OTHER PUBLICATIONS

"Differential modulation of tissue function and therapeutic potential selective inhibitors of cyclic nucleotide phosphodiesterase isoenzymes", C. David Nicholson, R.A. John Challiss and Mohammed Shahid, 1991, Elsevier Science Publishers Ltd. (UK), TIPS 12:19–27.

"Phosphodiesterase inhibitors: new opportunities for the treatment of asthma", Theodore J. Torphy, Bradley J. Undem, Thorax 1991; 46:512–523.

"Novel phosphodiesterase inhibitors for the therapy of asthma", Theodore J. Torphy, George P. Livi and Siegried B. Christensen, DN&P 6(4), May 1993 pp. 203–214.

"Assay of cyclic nucleotide phosphodiesterase and resolution of multiple molecular forms of the enzyme", W. Joseph Thompson, Wesley L. Terasaki, Paul M. Epstein, Samuel J. Strada, Advances in Cyclic Nucleotide Research, vol. 10, 1979, pp. 69–92.

"Identification, characterization and functional role of phosphodiesterase isozymes in human airway smooth muscle", Theodore J. Torphy, Bradley J. Undem, Lenora B. Cieslinski, Mark A. Luttmann, Martin L. Reeves and Douglas W.P. Hay, The Journal of Pharmacology and Experimental Therapeutics, 1993, vol. 265, No. 3, 1213–1223.

"The PDE IV family of calcium–independent phosphodiesterase enzymes", John A. Lowe III and John B. Cheng, Drugs of the Future, 1992, 17(9):799–807.

"Could isoenzyme–selective phosphodiesterase inhibitors render bronchodilator therapy redundant in the treatment of bronchial asthma?", Mark A. Giembycz, Biochemical Pharmacology, 1992, vol. 43, No. 10 pp. 2041–2051.

"Differential pharmacologic sensitivity of cyclic nucleotide phosphodiesterase isozymes from cardiac muscle, arterial and airway smooth muscle", Paul J. Silver, Linda T. Hamel, Mark H. Perrone, Ross G. Bently, Cynthia R. Bushover and Dale B. Evans, European Journal of Pharmacology, 150 (1988) 85–94, Elsevier.

"The pharmacology and therapeutic use of theophylline", Miles Weinberger, M.D., The Journal of Allergy and Clinical Immunology, vol. 73, No. 5, part 1, 525–544.

"Structure–Activity Relationships in a Series of 6–Thioxanthines with Bronchodilator and Coronary Dilator Properties", A.K. Armitrage, Janet Boswood and B.J. Large, Brit. J. Pharma. 1961, 17:196–207.

"The Synthesis of Some 6 Thioxanthines", K.R.H. Wooldrige and R. Slack, J. Chem. Soc. 1962, Annex IV:1863–1868.

Enoki et al Chemical Abstracts, vol. 85, No. 1 (Jul. 9, 1976) 5692s.

Enoki et al Chemical Abstracts, vol. 84, No. 25 (Jun. 21, 1976) 180299v.

Aida et al Chemical Abstracts, vol. 86, No. 7 (Feb. 14, 1977) 43746r.

Isomura et al., "Studies on the synthesis and anti–inflammatory activity of 2,6–Di–tert–butylphenols with a heterocyclic group at the 4–position.I", vol. 31, No. 9, pp. 3168–3178 (1983).

Chemical Abstracts 103:37354, 1985 (Nagarajan).

Chemical Abstracts 116:255335, 1992 (Bender).

Itaya, Tetrahedron Letters, vol. 23, No. 21 (1982), pp. 2203–2204.

Reitz, Journal of Organic Chemistry, vol. 55, No. 22 (Oct. 26, 1990), pp. 5761–5766.

Chemical Abstracts 88:51054, 1977 (Ninomiya).

Kazimier Czvil et al Chemical Abstracts, vol. 82 (19) May 12, 1975, Abstract #12358x.

Chemical Abstracts 114:246982, 1990 (Naruto).

"Controlled Interaction between Nucleic Acid Bases. Intramolecular Stacking Interactions between Two Adenine Rings", Nelson J. Leonard, et al.; Journal of the American Chemical Society, 95:12, Jun. 13, 1973, pp. 4010–4016.

Chemical Abstracts 92:6207, 1977 (Pirisino).

Ronald E. Weishaar, et al., Multiple molecular forms of cyclic nucleotide phosphodiesterase in cardiac and smooth muscle and in platelets, Biochemical Pharmacology, vol. 35, No. 5., pp. 787–800, 1986.

G.T. Rogers and T.L.V. Ulbricht, "Synthesis of 3–Methylisoguanine (6–amino–3–methylpurin–2(3H)–one)", J. Chem. Soc. (C), pp. 2364–2366 (1971).

Chemical Absracts 116:173873 (1979) Girshovich.

J. A. Montgomery, et al., "Synthesis of Potential Anticancer Agents. XIX. 2–Substituted $N^6$–Alkyladenines" (1959) J.A.C.S. vol. 81, pp. 3963–3967.

Chemical Abstracts 53:6243 (1957) Elion.

T. Fuji, et al. "3–Substituted Adenines. In Vitro Enzyme Inhibition and Antiviral Activity", Am. Chem. Soc., vol. 22, No. 2, pp. 126–129.

PDE IV INHIBITORS: "BIS-COMPOUNDS"

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these may actually contribute to its activity, only PDE inhibition may account for both the anti-inflammatory and bronchodilatory components. However, theophylline is known to have a narrow therapeutic index and a wide range of untoward side effects which are considered problematic.

Of the activities mentioned above, theophylline's activity in inhibiting cyclic nucleotide phosphodiesterase has recently received considerable attention. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-mono-phosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterases Inhibitors For The Therapy Of Asthma", Drug News & Prospective, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula (Formula A):

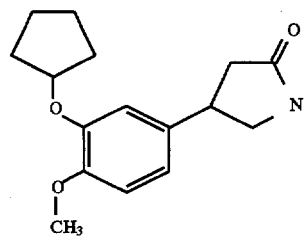

Formula A and of RO-20-1724, which has the following structural formula (Formula B):

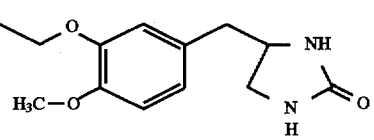

Formula B have been studied.

U.S. Pat. No. 4,308,278 discloses compounds of the Formula C:

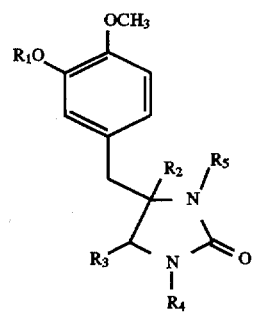

Formula C

Wherein $R_1$, is $(C_3-C_6)$ cycloalkyl or benzyl; each of $R_2$ and $R_3$ is hydrogen or $(C_1-C_4)$ alkyl; $R_4$ is $R_2$ or alkoxycarbonyl; and $R_5$ is hydrogen or alkoxycarbonyl.

Compounds of Formula D are disclosed in U.S. Pat. No. 3,636,039. These compounds are benzylimidazolidinones which act as hypertensive agents.

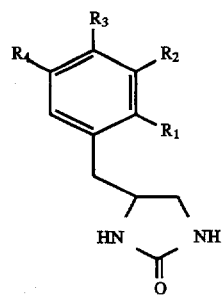

Formula D

Substituents $R_1-R_4$ in Formula D represent a variety of groups, including hydrogen and lower alkyl.

PCT publication WO 87/06576 discloses antidepressants of Formula E:

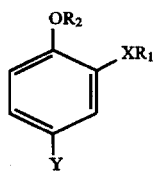

Formula E wherein $R_1$ is a polycycloalkyl group having from 7 to 11 carbon atoms; $R_2$ is methyl or ethyl; X is O or NH; and Y comprises of a mono-or by cyclic heterocyclic group with optional substituents.

Rolipram, which was initially studied because of its activity as an anti-depressant, has been shown to selectively inhibit the PDE IV enzyme and this compound has since become a standard agent in the classification of PDE enzyme subtypes.

There appears to be considerable therapeutic potential for PDE IV inhibitors. Early work focused on depression as a CNS therapeutic endpoint and on inflammation, and has subsequently been extended to include related diseases such as dementia and asthma. In-vitro, rolipram, R020-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV (and possibly PDE V) is present in all the major inflammatory cells in asthma including eosinophils, neutrophils, T-lymphocytes, macrophages and endothelial cells. Its inhibition causes down regulation of cellular activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous.

It appears that selective PDE IV inhibitors should be more effective with fewer side effects than theophylline. Clinical support has been shown for this hypothesis. Furthermore, it would be desirable to provide PDE IV inhibitors which are more selective than rolipram and therefore have a lower $P_{50}$ so as to reduce the amount of the agent required to effect PDE IV inhibition.

In recent years, several different compounds have been suggested as possible therapeutic compositions which achieve the desired PDE IV inhibition without the side effects alluded to above. However, these efforts have been chiefly directed to developing non-specific derivatives of particular classes of compounds, i.e. rolipram analogs, benzoxazoles, adenines, thioxanthines, etc. These efforts, however, have resulted in a myriad of compounds having a wide range of PDE IV $IC_{50}$s. Often, the general formulas disclosed yield several compounds which have poor levels of PDE IV inhibition and/or lack sufficient specificity. Consequently, these efforts often provide no assurance that any particular derivative within the formula will have the desired combination of high PDE IV inhibition and selectivity. The present invention addresses this need.

It is accordingly a primary object of the present invention to provide new compounds which have a superior PDE IV inhibitory effect as compared to rolipram and theophylline.

It is another object of the present invention to provide new compounds which act as effective PDE IV inhibitors with lower PDE III inhibition.

It is a further object of the present invention to provide new compounds which exhibit surprisingly greater selectivity with regard to their PDE IV inhibitory effects.

It is another object of the present invention to provide a method of treating a patient requiring PDE IV inhibition.

It is another object of the present invention to provide new compounds for treating disease states associated with abnormally high physiological levels of cytokines, including tumor necrosis factor.

It is another object of the present invention to provide a process of synthesizing the new compounds of this invention.

SUMMARY OF THE INVENTION

With the above and other objects in view, one aspect of the invention includes PDE IV inhibiting compounds containing a multi-ring system(s) with a substitution pattern that yields compounds having a high degree of selective PDE IV inhibition and an $IC_{50}$ below that of rolipram and theophylline. The present invention thus includes compounds of Formula I:

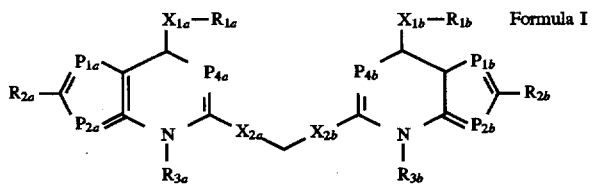

Formula I its pharmaceutically acceptable salts, hydrochloride salts or prodrug forms thereof, wherein:

$X_{1a}$, $X_{1b}$ are independently selected from —NH and —N-lower alkyl;

$X_{2a}$, $X_{2b}$ are optionally present and are independently selected from S(O)n, O, $CH_2$, and NH;

$P_{1a}$, $P_{1b}$, $P_{2a}$, $P_{2b}$, $P_{4a}$, and $P_{4b}$ are independently selected from N, or CH;

$R_{1a}$, $R_{1b}$, $R_{2a}$, $R_{2b}$, $R_{3a}$ and $R_{3b}$ are independently selected from H, $C_1$–$C_6$ alkyl, $C_3$–$C_6$ branched alkyl, $C_3$–$C_6$ cycloalkyl, said alkyl groups being optionally substituted with 1–3 groups selected from halogen, aryl or heteroaryl, said aryl or heteroaryl being optionally substituted with hydroxy, alkoxy, cycloalkoxy, halogen, alkyl, or cycloalkyl; and n is an integer from 0 to 2.

The present invention also provides pharmaceutically acceptable salts and prodrug forms of the compounds of Formula I. Also provided in the present invention is a method of effecting PDE IV inhibition in mammals by administering compounds of Formula I.

The present invention further provides a process for the synthesis of the compounds of Formula I. The process is described in Scheme I below:

Scheme I

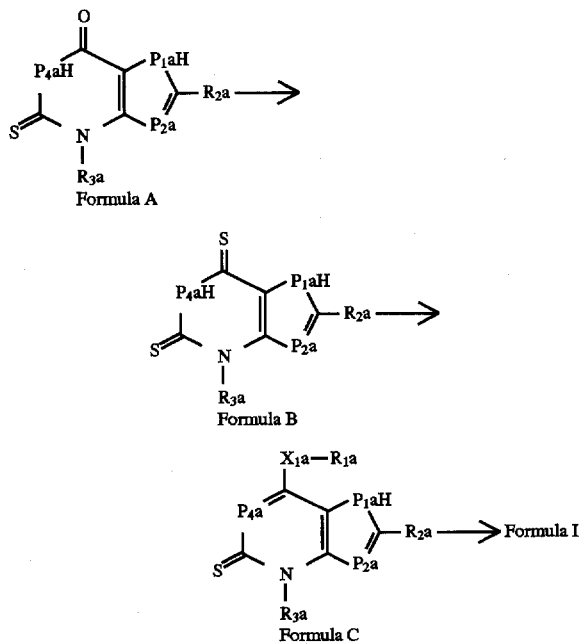

Formula A

Formula B

Formula C wherein:

$X_{1a}$ is selected from —NH and N-lower alkyl;

$X_{2a}$ is selected from a bond, S(O)n, O, $CH_2$, and NH;

$P_{1a}$, $P_{2a}$ and $P_{4a}$ are independently selected from N, or CH;

$R_{1a}$, $R_{2a}$ and $R_{3a}$ are independently selected from H, $C_1-C_6$ alkyl, $C_3-C_6$ branched alkyl, $C_3-C_6$ cycloalkyl, said alkyl groups being optionally substituted with halogen, aryl or heteroaryl groups being optionally substituted with hydroxy, $C_1-C_4$-alkoxy, $C_3-C_6$ cycloalkoxy; and n is an integer from 0–2.

Compounds of Formula C' having the structure:

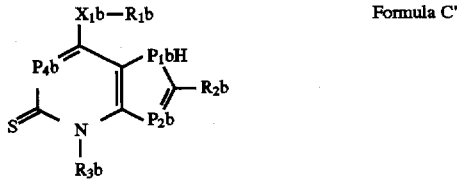

Formula C' can also be synthesized by the reaction process in Scheme I, wherein $X_{1b}$, $P_{1b}$, $P_{2b}$, $P_{4b}$, $R_{1b}$, $R_{2b}$, and $R_{3b}$ are as defined under the description of Formula I. Two molecules of a compound of Formula C or C', shown above, are reacted to form one molecule of the compound of Formula I, as depicted by the synthetic Scheme I. The substituents $X_{1a}$, $X_{1b}$, $X_{2a}$, $X_{2b}$, $P_{1a}$, $P_{1b}$, $P_{2a}$, $P_{2b}$, $P_{4a}$, $P_{4b}$, $R_{1a}$, $R_{1b}$, $R_{2a}$, $R_{2b}$, $R_{3a}$ and $R_{3b}$ are as defined earlier under the description of Formula I above and n is an integer from 0 to 2.

DETAILED DESCRIPTION OF THE INVENTION

The present invention includes PDE IV inhibiting compounds having selective PDE IV inhibition and an $IC_{50}$ below that of rolipram.

The present invention thus includes compounds of Formula I:

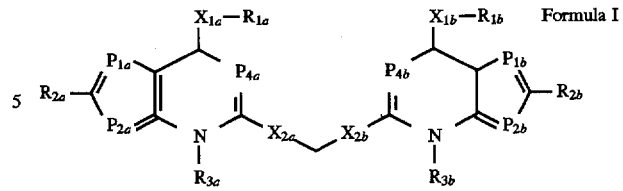

Formula I its pharmaceutically acceptable salts, hydrochloride salts or prodrug forms thereof, wherein:

$X_{1a}$, $X_{1b}$ are independently selected from —NH and —N-lower alkyl;

$X_{2a}$, $X_{2b}$ are optionally present and are independently selected from S(O)n, O, $CH_2$, and NH;

$P_{1a}$, $P_{1b}$, $P_{2a}$, $P_{2b}$, $P_{4a}$, and $P_{4b}$ are independently selected from N, or CH;

$R_{1a}$, $R_{1b}$, $R_{2a}$, $R_{2b}$, $R_{3a}$ and $R_{3b}$ are independently selected from H, $C_1-C_6$ alkyl, $C_3-C_6$ branched alkyl, $C_3-C_6$ cycloalkyl, said alkyl groups being optionally substituted with 1–3 groups selected from halogen, aryl or heteroaryl group(s), said aryl and heteroaryl group(s) being optionally substituted with hydroxy, alkoxy, cycloalkoxy, halogen, alkyl, or cycloalkyl; and n is an integer from 0 to 2.

Preferred compounds of the present invention are those wherein:

$X_{1a}$ and $X_{1b}$ are independently selected from —NH and —$NCH_3$;

$X_{2a}$ and $X_{2b}$ are each —S—, $P_{1a}$, $P_{1b}$, $P_{2a}$, $P_{4a}$ and $P_{4b}$ are each N; $R_{1a}$ and $R_{1b}$ are independantly selected from $C_3-C_5$ cycloalkyl and —$CH_2$-heteroaryl;

$R_{2a}$ and $R_{2b}$ are each cyclopropyl; and $R_{3a}$ and $R_{3b}$ are independently selected from —$C_1-C_6$ Further preferred compounds of the present invention include compounds wherein:

$X_{1a}$ and $X_{1b}$ are independently selected from NH and $NCH_3$;

$X_{2a}$ and $X_{2b}$ are each —S—;

$P_{1a}$, $P_{1b}$, $P_{2a}$, $P_{2b}$, $P_{4a}$ and $P_{4b}$ are each N;

$R_{1a}$ and $R_{1b}$ are independently selected from cyclopentyl and —$CH_2$-pyridyl;

$R_{2a}$ and $R_{2b}$ are each cyclopropyl; and $R_{3a}$ and $R_{3b}$ are each propyl.

Particularly preferred compounds of the present invention include:

1. 2,2'-[methylenebis(thio)]bis-[8-cyclopropyl-3-propyl-6-(4-pyridylmethylamino)-3H-purine] tetrahydrochloride dihydrate
2. 2,2'-[methylenebis(thio)]bis-[6-cyclopentylamino-8-cyclopropyl-3-propyl-3H-purine]dihydrochloride.

Provided in the present invention are methods of effecting PDE IV inhibition in mammals by administering a compound of Formula I. Also provided in the present invention are methods of treating a mammal suffering from a disease state selected from a group consisting of allergies, inflammation, atopic diseases such as asthma, and rhinitis, comprising administering a compound of claim 1.

Another aspect of the present invention provides a process, depicted in Scheme I, for the syntheses of the compounds of Formula I having the structure:

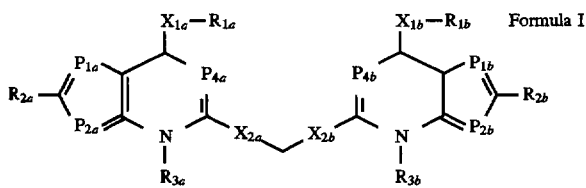

Formula I its pharmaceutically acceptable salts, hydrochloride salts, or prodrug forms thereof, wherein:

$X_{1a}$, $X_{1b}$ are independently selected from —NH and —N-lower alkyl;

$X_{2a}$, $X_{2b}$ are optionally present and are independently selected from S(O)n, O, CH$_2$, and NH;

$P_{1a}$, $P_{1b}$, $P_{2a}$, $P_{2b}$, $P_{4a}$, and $P_{4b}$ are independently selected from N, or CH;

$R_{1a}$, $R_{1b}$, $R_{2a}$, $R_{2b}$, $R_{3a}$ and $R_{3b}$ are independently selected from H, $C_1$–$C_6$ alkyl, $C_3$–$C_6$ branched alkyl, $C_3$–$C_6$ cycloalkyl, said alkyl groups being optionally substituted with halogen, aryl or heteroaryl group(s), said aryl and heteroaryl group(s) being optionally substituted with hydroxy, alkoxy, cycloalkoxy, halogen, alkyl, or cycloalkyl; and n is an integer from 0 to 2;

which comprises:

(a) treating a compound of Formula A:

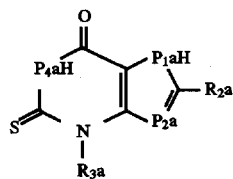

Formula A wherein $P_{1a}$, $P_{2a}$, $P_{4a}$ and $R_{3a}$ are as defined above, with an effective amount of a thionating agent to produce a compound of Formula B:

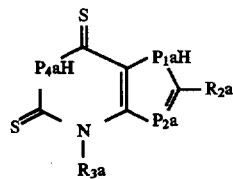

Formula B (b) treating a compound of Formula B, with an aminating agent under conditions effective to produce a compound of Formula C:

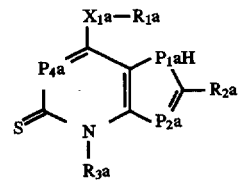

wherein $X_{1a}$, $R_{1a}$, $P_{1a}$, $P_{2a}$, $R_{2a}$, $R_{3a}$ and $P_{4a}$ are as defined above; and (c) treating a compound of Formula C with silica gel under conditions effective to produce a compound of Formula I.

Compounds of Formula C' having the structure:

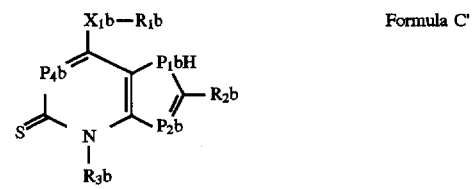

Formula C' can also be synthesized by the reaction process inn Scheme I, wherein $X_{1b}$, $P_{1b}$, $P_{2b}$, $P_{4b}$, $R_{1b}$, $R_{2b}$, and $R_{3b}$ are as defined under the description of Formula I. Two molecules of a compound of Formula C or C', shown above, are reacted to form one molecule of the compound of Formula I, as depicted by the synthetic Scheme I. The substituents $X_{1a}$, $X_{1b}$, $X_{2a}$, $X_{2b}$, $P_{1a}$, $P_{1b}$, $P_{2a}$, $P_{2b}$, $P_{4a}$, $P_{4b}$, $R_{1a}$, $R_{4b}$, $R_{1a}$, $R_{2a}$, $R_{2b}$, $R_{3a}$ and $R_{3b}$ are as defined earlier under the description of Formula I above and n is an integer from 0 to 2.

In a preferred embodiment is provided a process to make compounds of Formula I, wherein $X_{1a}$ and $X_{1b}$ are independently selected from —NH and —NCH$_3$;

$X_{2a}$ and $X_{2b}$ are each —S—;

$P_{1a}$, $P_{1b}$, $P_{2a}$, $P_{2b}$, $P_{4a}$ and $P_{4b}$ are each N;

$R_{1a}$ and $R_{1b}$ are independently selected from $C_4$–$C_5$ cycloalkyl and —CH$_2$-heteroaryl;

$R_{2a}$ and $R_{2b}$ are each cyclopropyl; and $R_{3a}$ and $R_{3b}$ are independently selected from —$C_1$–$C_6$ alkyl.

In a further preferred embodiment is provided a process to make compounds of Formula I selected from 2,2'-[methylenebis(thio)]bis-[8-cyclopropyl-3-propyl-6-(4-pyridylmethylamino)-3H-purine]tetrahydrochloride dihydrate;

2,2'-[methylenebis(thio)]bis-[6-cyclopentylamino-8-cyclopropyl-3-propyl-3H-purine]dihydrochloride.

The process to make compounds of Formula I is schematically depicted in Scheme I as follows:

Scheme I

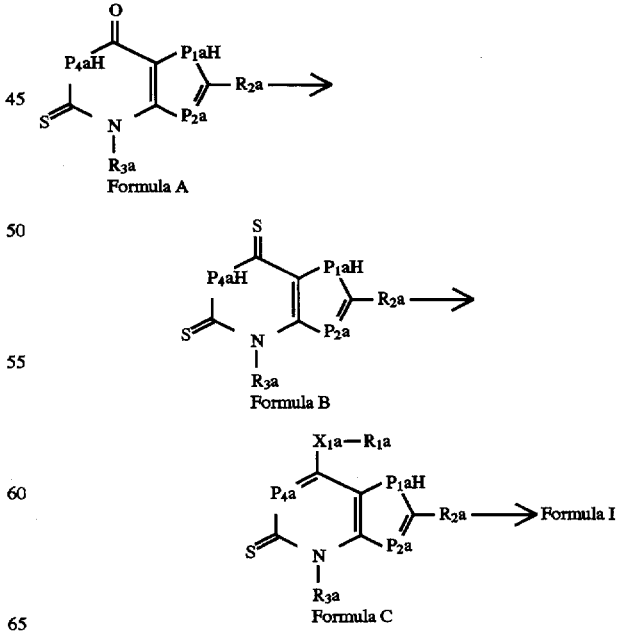

wherein:

$X_{1a}$, $X_{1b}$, $X_{2a}$, $X_{2b}$, $P_{1a}$, $P_{1b}$, $P_{2a}$, $P_{2b}$, $P_{4a}$, $P_{4b}$, $R_{1a}$, $R_{1b}$, $R_{2a}$, $R_{2b}$, $R_{3a}$, and n are as defined above.

As defined herein "alkyl" represents a $C_1$–$C_8$ straight chain alkyl, $C_3$–$C_8$ branched alkyl or $C_3$–$C_8$ cycloalkyl group. As defined herein, "lower alkyl" represents —$C_1$–$C_4$ straight chain alkyl, —$C_3$–$C_5$ branched alkyl, or —$C_3$–$C_8$ cycloalkyl group. A "heteroaryl" group, as defined herein, represents a $C_5$–$C_{10}$ mono or bicyclic ring system which can be saturated, unsaturated or aromatic, having from 1 to 3 heteroatoms selected from N, O and S.

Representative examples of a "heteroaryl" group are pyrrole, pyridine (pyridyl), oxazole, adenines, benzoxazole, and the like.

The present invention also includes pharmaceutically acceptable salts and prodrugs of all the compounds of Formula I. Pharmaceutically acceptable salts include hydrochlorides, cholines and others.

In another embodiment of the present invention is provided a method of effecting PDE IV inhibition in mammals which comprises administering a compound of Formula I. In yet another embodiment of the present invention is provided a method of treating a mammal suffering from a disease state selected from a group consisting of allergies, inflammation, atopic diseases such as asthma, and rhinitis, comprising administering a compound of Formula I.

Methods of Syntheses

The compositions of the present invention can be prepared using standard organic methods. Details concerning preparing some of the preferred compounds are provided in the Examples section below.

Methods of Treatment

In view of the high degree of selective PDE IV inhibition, the compounds of the present invention can be administered to anyone requiring PDE IV inhibition. Administration may be accomplished orally, topically, by suppository, inhalation or insufflation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods. Alternatively, alkali and alkaline earth metal salts are prepared by reaction of the compounds of the invention with the appropriate base via a variety of known methods. For example, the sodium salt of the compounds of the invention can be prepared via reacting the compound with sodium hydride.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavorings agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used for formulate oral dosage forms, are described in the *Handbook of Pharmaceutical Excipients*, American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Forms: Disperse Systems*, (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

The present invention is further related to a method for the treatment of allergic and inflammatory disease which comprises administering to a mammal in need thereof an effective amount of the compounds of the present invention.

The present invention is also related to a method for the mediation or inhibition of the enzymatic or catalytic activity of PDE IV activity in mammals, particularly humans, which comprises administering an effective amount of the above-described compounds of the invention to a mammal in need of PDE IV inhibition.

The compounds of the present invention may find use in the treatment of other disease states in humans and other mammals, such as in the treatment of disease states associated with a physiologically detrimental excess of tumor necrosis factor (TNF). TNF activates monocytes, macrophages and T-lymphocytes. This activation has been implicated in the progression of Human Immunodeficiency Virus (HIV) infection and other disease states related to the production of TNF and other cytokines modulated by TNF.

The following examples illustrate various aspects of the present invention, and are not to be construed to limit the claims in any manner whatsoever.

EXAMPLE 1

S,S'-methylene-bis(2-(8-cyclopropyl-3-propyl-6-(4-pyridylmethylamino)-2-Thio-3 H-purine)) tetrahydrochloride (i) 8-Cyclopropyl-3-propyl-2,6-dithioxanthine In a 5 L 3-necked flask fitted with a mechanical stirrer and a condenser with a drying tube were placed 2.2 L of pyridine and 8-cyclopropyl-3-propyl-2-thio-6-oxoxanthine (220 g, 0.88 mol). Phosphorus pentasulfide (236 g, 1.06 mol) was added and the mixture was heated under reflux for 5 hours and stored overnight at room temperature. The reaction mixture was cooled to 5°–10° and 3N aqueous sodium hydroxide (770 ml) was added over 1.5 hours with stirring. Stirring was continued for 30 minutes after removal of the cooling bath and the precipitated product was collected by suction filtration. The filter cake was washed successively with pyridine (300 ml) and four 300 ml portions of tetrahydrofuran. The solvents are evaporated in vacuo and the solid residue was stirred with water (750 ml), filtered and washed with water. The crude product was dissolved in 1.7 L of 1N sodium hydroxide and stirred with 15 g of Darco G-60. The charcoal was filtered and the treatment was repeated with a fresh portion of charcoal. The solution was acidified to pH 1.5 with 6 N hydrochloric acid and the pale yellow precipitate was collected. The solid was dissolved again in 1.7 L of 1N sodium hydroxide and treated successively with two portions of charcoal as above. The solution was acidified and the precipitate was collected and washed with water. After drying to constant weight at 54° C. under vacuum, there was obtained 128 g (56%) of the title compound, mp over 245° C.

(ii) 8-Cyclopropyl-3,7-dihydro-3-propyl-6-(4-pyridylmethylamino)-2H-purine-2-thione 5.33 g (20 mmoles) of 8-cyclopropyl-3-n-propyl-2,6-dithioxanthine and 21.3 ml (200 mmoles) of 95% 4-picolylamine were heated under argon to 150°–5° C. After 14 hours the cooled solution was poured into 100 ml of water, acidified with 19 ml of 10N HCl to pH 6, where an orange colored gum was formed. With sodium bicarbonate the mixture was neutralized to pH 7. With time the gum crystallized and the solid is collected and washed. The residue was suspended in acetone and the crystals collected: 3.92 (57.6%) of crude product. The filtrate was evaporated to dryness, dissolved in 40 ml of 0.5N NaOH, extracted 4 times with methylene chloride, and acidified again with 5N HCl to pH 6. Again the gum crystallized over 48 hours and the mixture was neutralized to pH 7 with bicarbonate and the solid collected: 1.75 g (25.7%) of crude product. Both parts were dissolved in 30 ml of methylene chloride and filtered through 30 g of silicagel in a column 150 mg (2.8%) of starting material was recovered first, then 5.04 g (74.0%) of product was recovered with 5% of methanol, which was dissolved in 32 ml of 1N HCl, treated with 250 mg of charcoal, filtered, and neutralized with 7.5 ml of 2N NaOH and sodium bicarbonate solution to pH 7–8. The water phase was decanted from the gum and the latter washed with water and crystallized from acetone: 4.08 g (59.9%) of thioisoguanine with mp 204°–210° C. with decomposition.

(iii) S,S'-methylene-bis(6-cyclopentylamino-8-cyclopropyl-3-propyl-2-thio-3H-purine) dihydrochloride 15 5.39 g (17 mM) of $N^6$-cyclopentyl-8-cyclopropyl-3-propyl-2-thioisoguanine were dissolved in 60 ml of dichloromethane and stirred for 24 hr at 25° C. with 6 g of silicagel. The mixture was purified by chromatography on silicagel eluting with dichloromethane, to give the free base of the title compound (4.24g), which was dissolved in 30 ml methanol, treated with 16.9 ml of 1 M methanolic HCL and evaporated to dryness. Crystallization and recrystallization from dichloromethane-acetone gave 1.04 g of the title compound, mp 278°–80° C.

Elemental analysis for $C_{33}H_{48}Cl_2N_{10}S_2$ Calc. C 55.06 H 6.72 Cl 9.85 N 19.46 S 8.91 Found C 54.84 H 6.71 Cl 10.14 N 19.05 S 8.92

EXAMPLE 2

S,S'-methylene-bis(2-(8-cyclopropyl-3-propyl-6-(4-pyridylmethylamino)-2-thio-3H-purine)) tetrahydrochloride 5.67 g (16.7 mM) of 8-cyclopropyl-$N^6$-(4-picolyl)-3-propyl-2-thio-isoguanine were dissolved in 30 ml of dichloromethane and stirred for 24 hr at 25° C. with 3 g of silicagel. The mixture was purified by chromatography on a silicagel column eluting with dichloromethane, to give the crude free base of the title compound (5.04 g), which was dissolved in 40 ml of methanol, treated with 30 ml of 1M methanolic HCl and evaporated to dryness. The residue was crystallized from dichloromethane and recrystallized from isopropanol to give the title compound (1.09 g), mp 198°–210° C. (dec).

Elemental analysis for $C_{35}H_{40}N_{12}S_2$. 3.8 HCl. 2.2 $H_2O$ Calc C 48.23 H 5.58 Cl 15.46 N 19.28 O 4.09 S 7.36 Found C 48.08 H 5.58 Cl 15.69 N 19.13 O 4.39 S 7.43

Enzyme Isolation Protocol
Protocols for PDE III and PDE IV inhibition activity are set forth below Type III Phosphodiesterase The Type III PDE is isolated from human platelets using a procedure similar to that previously described by Weishaar, R. E.; Burrows, S. D.; Kobylarg, D. C., Quade, N. M.; Evans, D. B., Biochem. Pharmacol., 35:787, 1986. Briefly, 1–2 units of platelets are suspended in an equal volume of buffer (20 mM Tris-HCl, pH 7.5, containing 2 mM magnesium acetate, 1 mM dithiothreitol, and 5 mM $Na_2$ EDTA). The protease inhibitor phenyl methyl-sulfonyl fluoride (PMSF) is also included in this buffer at a final concentration of 200 µM. The suspension is homogenized using a polytron and the homogenate centrifuged at 100,000 x g for 60 minutes. This and all subsequent procedures are performed at 0°–4° C. The supernatant is then filtered through four layers of gauze and applied to a DEAE-Trisacryl M column, previously equilibrated with buffer B (20 mM Tris-HCl, pH 7.5, containing 1 mM magnesium acetate, 1 mM dithiothreitol and 200µM PMSF). After application of the sample, the column is washed with several bed volumes of buffer B, after which the different forms of PDE are eluted from the column using two successive linear NaCl gradients (0.05–0.15M, 300 ml total; 0.15–0.40M, 200 ml total). Five milliliter fractions are collected and assayed for cyclic AMP and cyclic GMP PDE activity. Fractions containing PDE III activity are pooled and dialyzed overnight against 4 liters of buffer B. The dialyzed PDE III is then concentrated to 10% of the original volume, diluted to 50% with ethylene glycol monoethyl ether and stored at −20° C. PDE III can typically be retained for up to four weeks with little or no loss of activity.

Measuring Type III PDE Activity

Enzyme activity is assessed by measuring the hydrolysis of [$^3$H]-cyclic AMP, as described by Thompson, W. J., Teraski, W. L., Epstein, P. N., Strada, S. J.: Adv. Cyclic Nucleotide Res. 10:69, 1979. The cyclic AMP concentration used in this assay is 0.2 µM, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

Type IV Phosphodiesterase

Enzyme Isolation Protocol

The Type IV PDE is isolated from bovine tracheal smooth muscle using a procedure similar to that previously described by Silver, P. J., et al.: Eur. J. Pharmacol. 150:85, 1988. (1). Briefly, smooth muscle from bovine trachea is minced and homogenized using a polytron in 10 volumes of an extraction buffer containing 10 mM Tris-acetate (pH 7.5), 2 mM magnesium chloride, 1 mM dithiothreitol and 2,000 units/ml of aprotinin. This and all subsequent procedures are performed at 0°–4° C. The homogenate is sonicated and then centrifuged at 48,000×g for 30 minutes. The resulting supernatant is applied to a DEAE Trisacryl M column previously equilibrated with sodium acetate and dithiothreitol. After applications of the sample, the column is washed with sodium acetate/dithiothreitol, after which the different forms of PDE are eluted from the column using a linear Tris-HCl/NaCl gradient. Fractions containing Type IV PDE are collected, dialyzed and concentrated to 14% of the original volume. The concentrated fractions are diluted to 50% with ethylene glycol and stored at −20° C.

Measuring Type IV PDE Activity

Enzyme activity is assessed by measuring the hydrolysis of [$^3$H]-cyclic AMP, as described by Thompson, W. J., et al.: Adv. Cyclic Nucleotide Res. 10:69, 1979. The cyclic AMP concentration used in this assay is 0.2 µM, which approximates to the $K_m$ value. Protein concentration is adjusted to ensure that no more than 15% of the available substrate is hydrolyzed during the incubation period.

test compounds are dissolved in dimethyl sulfoxide (final concentration of 2.5%). This concentration of dimethyl sulfoxide inhibits enzyme activity by approximately 10%.

Measuring Type V PDE Activity

Enzyme Isolation Protocol

The Type V PDE is isolated using a procedure similar to that previously described by Weishaar et al., Hypertension 15:528, (1990). Briefly, 1–2 units of platelets are suspended in an equal volume of buffer A (20 mM Tris-HCl, pH 7.5, containing 2 mM magnesium acetate, 1 mM dithiothreitol, and 5 mM Na$_2$EDTA) using a polytron. The proteinase inhibitor phenylmethylsulfonyl fluoride (PMSF) are also included in this buffer at a final concentration of 200 uM. This and all subsequent procedures are performed at 0°–4° C. The homogenate is then centrifuged at 100,000 rpm for 60 minutes. The supernatant is then removed and filtered through four layers of gauze and applied to a DEAE-Trisacryl M column. The column is washed with several bed volumes of buffer B (20 mM Tris-HCl, pH 7.5, containing 2 mM magnesium acetate, 1 mM diothiothreitol, and 200 µM PMSF) and eluted by two successive linear NaCl gradients (0.05–0.15M, 300 ml total; 0.15–0.40M, 200 ml total). Five ml fractions are collected and assayed for cyclic AMP and cyclic GMP PDE activity. Fractions that contain PDE V are pooled and dialyzed overnight against 4 L of buffer C (20 mM Tris-HCl, pH 7.5, containing 2 mM magnesium acetate and proteinase inhibitors). The dialyzed PDE V is then concentrated to 10% of the original volume, diluted to 50% with ethylene glycol monoethyl ether and stored at −20° C. PDE V can typically be retained for up to four weeks with little or no loss of activity.

Measuring Type V PDE Activity:

Enzyme activity is assessed by measuring the hydrolysis of [$^3$H]-cyclic GMP, as described by Thompson et al. (Thompson, W. J., Teraski, W. L., Epstein, P. N., Strada, S. J.: Adv. Cyclic Nucleotide Res. 10:69, 1979). The cyclic GMP concentration used in this assay is 0.2 uM, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%. The reference Type V PDE inhibitor zaprinast is evaluated with each assay.

The compounds are tested over concentration range: 0.1, 1, 10, 100 uM (n=1), and IC$_{50}$ determinations are made using 5 appropriate concentrations (n=2).

As can be seen from the foregoing, the compositions of the present invention are also potent inhibitors of PDE V in mammals. Such activity is useful in the medical arts to reduce smooth muscle cell proliferation and increase pulmonary vasodilation. In certain aspects of the invention, the compounds demonstrate a combination of selective PDE IV and PDE V inhibition and can be used in diseases such as restenosis and related diseases. Such aspects, of course, include administering an effective amount of a compound of the present invention possessing said combination of PDE IV and V inhibitory activities to a mammal in need of such therapy.

Following the above procedures, the PDE III, PDE IV and PDE V inhibition for the compounds of Examples 1 and 2, Theophylline and Rolipram were tested and compared. The results are shown the Table I below:

TABLE I

| EXAMPLE | PDE IV IC$_{50}$(µM) | PDE III IC$_{50}$(µM) | PDE V IC$_{50}$(µM) |
|---|---|---|---|
| 1 | 0.029 | 135.94 | 19.0 |
| 2 | 0.440 | 56.9 | 0.2 |
| Rolipram | 3.7 | 620 | 500 |
| Theophylline | 321 | 380 | 750 |

As can be seen from the foregoing, the inventive compounds provide high levels of PDE-IV inhibition and low levels of PDE-III inhibition. In all cases, the PDE-IV IC$_{50}$ values were below that of rolipram and the PDE-III and PDE V values were all at levels which are associated with low levels of inhibition.

While the invention has been illustrated with respect to the production and use of particular compounds, it is apparent that variations and modifications of the invention can be made without departing from the spirit or scope of the invention.

The present invention also provides a method of effecting selective PDE IV inhibition in mammals requiring the same, which comprises administering an effective amount of a compound of Formula I, its pharmaceutically acceptable salts, hydrochloride salts or prodrug forms thereof.

Also provided in the present invention is a method of treating a mammal suffering from a disease state selected from a group consisting of asthma, allergies, inflammation, dementia, atopic diseases, rhinitis, and disease states associated with abnormally high physiological levels of cytokine, comprising administering an effective amount of a compound of Formula I, its pharmaceutically acceptable salts, hydrochloride salts or prodrug forms thereof.

We claim:

1. A compound of Formula I,

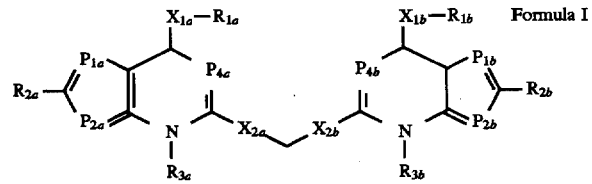

its pharmaceutically acceptable salts, wherein:

$X_{1a}$, $X_{1b}$ are independently selected from —NH and —N-lower alkyl;

$X_{2a}$, $X_{2b}$ are optionally present and are independently selected from S(O)n, O, CH$_2$, and NH;

$P_{1a}$, $P_{1b}$, $P_{2a}$, $P_{2b}$, $P_{4a}$, and $P_{4b}$ are N;

$R_{1a}$, $R_{1b}$, $R_{2a}$, $R_{2b}$, $R_{3a}$ and $R_{3b}$ are independently selected from H, $C_1$–$C_6$ alkyl, $C_3$–$C_6$ branched alkyl, $C_3$–$C_6$ cycloalkyl, said alkyl groups being optionally substituted with halogen, aryl or pyridyl group(s), said aryl and pyridyl group(s) being optionally substituted with hydroxy, alkoxy, cycloalkoxy, halogen, alkyl, or cycloalkyl; and n is an integer from 0 to 2.

2. A compound of claim 1, wherein:

$X_{1a}$ and $X_{1b}$ are independently selected from —NH and —NCH$_3$;

$X_{2a}$ and $X_{2b}$ are each —S—;

$P_{1a}$, $P_{1b}$, $P_{2a}$, $P_{2b}$, $P_{4a}$ and $P_{4b}$ are each N;

$R_{1a}$ and $R_{1b}$ are independently selected from $C_4$–$C_5$ cycloalkyl and —CH$_2$-pyridyl;

$R_{2a}$ and $R_{2b}$ are each cyclopropyl; and $R_{3a}$ and $R_{3b}$ are independently selected from —$C_1$–$C_6$ alkyl.

3. A compound of claim 2 wherein $X_{1a}$ and $X_{1b}$ are independently selected from NH and NCH$_3$;

$X_{2a}$ and $X_{2b}$ are each —S—;

$P_{1a}$, $P_{1b}$, $P_{2a}$, $P_{2b}$, $P_{4a}$ and $P_{4b}$ are each N;

$R_{1a}$ and $R_{1b}$ are independently selected from cyclopentyl and —CH$_2$-pyridyl;

$R_{2a}$ and $R_{2b}$ are each cyclopropyl; and $R_{3a}$ and $R_{3b}$ are propyl.

4. A compound of claim 3 selected from 2,2'-[methylenebis(thio)]bis-[8-cyclopropyl-3-propyl-6-(4-pyridylemthylamino)-3H-purine]tetrahydrochoride dilhydrate[S,S'-methylene-bis-(2-(8-cyclopropyl-3-propyl-6-(4-pyridymethylamino)-2-thio-3-H-purine)) tetrahydrochloride]; and 2,2'-[methylenebis(thio)]bis-[6-cyclopentylamino-8-cyclopropyl-3-propyl-3H-purine]dihydrochlride[S,S'-methylene-bis(6-cyclopentyl-8-cyclopropyl-3-propyl-2-thio-3H-purine)dihydrochloride].

5. A compound of claim 2 wherein $R_{1a}$ and $R_{1b}$ are each —CH$_2$-pyridyl.

6. A pharmaceutical composition of a compound of claim 1, further comprising a pharmaceutically acceptable carrier.

7. A pharmaceutical composition of a compound of claim 2, further comprising a pharmaceutically acceptable carrier.

8. A pharmaceutical composition of a compound of claim 3, further comprising a pharmaceutically acceptable carrier.

9. A pharmaceutical composition of a compound of claim 4, further comprising a pharmaceutically acceptable carrier.

10. A method of treating a mammal suffering from a disease state selected from a group consisting of allergies, inflammation, atopic diseases selected from the group consisting of asthma and rhinitis, comprising administering a compound of claim 2.

11. A method of treating a mammal suffering from a disease state selected from a group consisting of allergies, inflammation, atopic diseases selected from the group consisting of asthma and rhinitis, comprising administering an effective amount of a compound of claim 3.

12. A method of treating a mammal suffering from a disease state selected from a group consisting of allergies, inflammation, atopic diseases selected from the group consisting of asthma and rhinitis, comprising administering an effective amount of a compound of claim 4.

13. A method of effecting PDE IV inhibition in mammals which comprises administering a compound of claim 1.

14. A method of effecting PDE IV inhibition in mammals which comprises administering a compound of claim 2.

15. A method of effecting PDE IV inhibition in mammals which comprises administering a compound of claim 3.

16. A method of effecting PDE IV inhibition in mammals which comprises administering a compound of claim 4.

17. A method of treating a mammal suffering from a disease state selected from a group consisting of allergies, inflammation, atopic diseases selected from the group consisting of asthma and rhinitis, comprising administering a compound of claim 1.

* * * * *